United States Patent [19]
Winkelmann et al.

[11] 4,053,482
[45] Oct. 11, 1977

[54] 1-METHYL-2-(SUBSTITUTED THIOMETHYL)-5-NITRO-IMIDAZOLES

[75] Inventors: Erhardt Winkelmann, Kelkheim, Taunus; Wolfgang Raether, Dreieichenhain, both of Germany

[73] Assignee: Hoechst Aktiengesellschaft, Frankfurt am Main, Germany

[21] Appl. No.: 674,429

[22] Filed: Apr. 7, 1976

[30] Foreign Application Priority Data

Apr. 9, 1975 Germany .............................. 2515522
Apr. 9, 1975 Germany .............................. 2515515

[51] Int. Cl.$^2$ .................. C07D 233/94; C07D 405/12; C07D 409/12; A61K 31/415
[52] U.S. Cl. ................................ 548/336; 424/273 R; 548/339
[58] Field of Search ......................... 260/309; 424/273

[56] References Cited

U.S. PATENT DOCUMENTS

| 3,696,116 | 10/1972 | Jeanmart et al. | 260/309 |
| 3,773,781 | 11/1973 | Carlson et al. | 260/309 |
| 3,922,277 | 11/1975 | Winkelmann et al. | 260/309 |
| 3,962,454 | 6/1976 | Winkelmann et al. | 260/309 |
| 3,984,426 | 10/1976 | Winkelmann et al. | 260/309 |

OTHER PUBLICATIONS

Tweit et al., Chem. Abst., 1974, vol. 80, No. 420p.

*Primary Examiner*—Natalie Trousoe
*Attorney, Agent, or Firm*—Curtis, Morris & Safford

[57] ABSTRACT

Certain 1-methyl-2-(substituted thiomethyl)-5-nitroimidazoles are described as well as a process for their manufacture. The compounds are suitable for the treatment of protozoal diseases, especially of trichomoniasis and of fungus diseases, especially dermatomycoses.

4 Claims, No Drawings

1-METHYL-2-(SUBSTITUTED THIOMETHYL)-5-NITRO-IMIDAZOLES 1-(2-Hydroxyethyl)-2-methyl-5-nitro-imidazole (Metronidazol) is known to be used for the treatment of protozoal diseases such as trichomoniasis and amebiasis.

The present invention relates to 1-methyl-2-(substituted thiomethyl)-5-nitro-imidazoles of the formula I

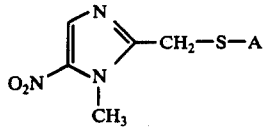
(I)

in which A stands either for the radical of the formula

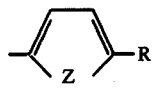

in which Z is oxygen or sulfur, and R is the nitro or cyano group, or A stands for the radical

in which R' is the methyl, ethyl, benzyl or phenyl group.

This invention further relates to a process for the manufacture of 1-methyl-2-(substituted thiomethyl)-5-nitro-imidazoles of formula I, which comprises either a. reacting a 1-methyl-2-substituted methyl-5-nitro-imidazole of the formula II

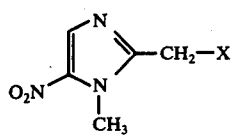

in which X stands for a halogen atom, such as a fluorine, chlorine, bromine or iodine atom, or an acyloxy group, such as the acetyloxy, propinyloxy, butyryloxy, benzoyloxy, nitrobenzoyloxy, toloyloxy group, or an arylsulfonyloxy group, such as benzenesulfonyloxy, toluenesulfonyloxy, nitrobenzene-sulfonyloxy, with a thio compound or an alkali metal or ammonium salt thereof of the formula III

 (III)

in which Y stands for a hydrogen atom, an alkali metal, especially sodium or potassium, or ammonium, and A stands for the radical (-/1)

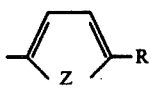

in which Z is an oxygen or sulfur atom, and R is the nitro or cyano group, or A stands for the radical (-/2)

in which R' is the methyl, ethyl, benzyl or phenyl group, or b. reacting 1-methyl-2-mercaptomethyl-5-nitro-imidazole of the formula IV

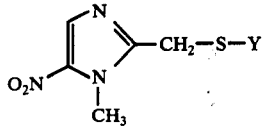
(IV)

in which Y is defined as above, with a halogenated compound of the formula V

 (V)

in which X' stands for a halogen atom, preferably chlorine, bromine or iodine, and A stands for the radical (-/1)

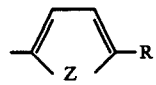

in which Z is the oxygen or sulfur atom, and R is the nitro or cyano group, or A stands for the radical (-/2)

in which R' is the methyl, ethyl, benzyl or phenyl group.

As starting substances of formula II, there may be mentioned, for example, 1-methyl-2-chloro-, -2-bromo-, -2-iodomethyl-5-nitro-imidazole, 1-methyl-2-acetyloxy-, -2-benzoyloxy-, -2-(4-nitrobenzoyl)oxy-, -2-toluenesulfonyloxy-methyl-5-nitroimidazole.

As starting substances of formula III/1, there are mentioned, for example, 5-nitro-, 5-cyano-furano-2-thiol, 5-nitro-, 5-cyano-thiophene-2-thiol; instead of the free thio compounds, the alkali metal or ammonium salts or mercaptan-yielding agents, for example isothiouronium salts, may also be used.

As starting compounds of formula III/2, there may be mentioned, for example, dithiocarbonic acid-O-methyl-, -O-ethyl-, -O-benzyl- or -O-phenyl ester. Instead of the free thio compounds, the alkali metal or ammonium salts thereof (xanthogenates) or mercaptan-yielding agents, for example isothiouronium salts may also be used.

As starting substances of formula IV, there may be mentioned, for example, 1-methyl-2-mercaptomethyl-5-nitro-imidazole or the alkali metal or ammonium salts thereof or mercaptan-yielding agents, for example isothiouronium salts.

As starting compound of formula V/1, there are mentioned, for example, 2-chloro-, 2-bromo-, 2-iodo-5-nitro-furan, —5—cyano-furan, 2-chloro-, 2-bromo-, 2-iodo-5-nitro-thiophene, -5-cyano-thiophene.

As starting substances of formula V/2, there are mentioned, for example, chloro-, bromo-thiocarbonic acid -O-methyl ester, -O-ethyl ester, -O-benzyl ester or -O-phenyl ester.

The two embodiments (a) and (b) of the process of the invention are advantageously carried out using equimolar amounts of each starting substance, advantageously in a solvent or distributing agent.

As solvents suitable for methods (a) and (b), there are mentioned any solvents which have a satisfactory dissolving power for the reaction components without showing chemical interactions therewith. Suitable solvents are, for example, alcohols, such as methanol, ethanol, propanol, isopropanol, butanol, methoxyethanol, ethoxyethanol; ketones such as acetone, methylethyl-ketone, methylbutyl-ketone; amides such as dimethylformamide, diethylformamide, dimethylacetamide; furthermore N-methyl-pyrrolidone, tetramethyl-urea, hexamethyl-phosphoric acid triamide, or dimethyl-sulfoxide.

The reaction temperatures may generally range from 0° to 100° C, preferably from 0° to 40° C. The reaction times depend on the temperature chosen and range from a few minutes to several hours.

When the free thio compounds of formula III are used, it is advantageous to employ an acid-binding agent, too. As acid-binding agents, there are mentioned bases, such as triethylamine or pyridine, alkaline agents, such as alkali metal and alkaline earth metal carbonates and bicarbonates, hydroxides and alkoxides, for example methoxides, ethoxides or butoxides.

The products of the invention are isolated according to the usual methods by separating the solvents used by distillation or diluting the reaction solution with water. The isolated products may optionally be purified by recrystallization from a suitable solvent or mixture of solvents.

The new compounds of formula I are well compatible and are suitable for the treatment of protozoal diseases in human beings and animals, especially of trichomoniases as caused, for example, by infections with Trichomonas vaginalis, or of fungus diseases, especially dermatomycoses as caused, for example, by Trichophyton mentagrophytes, Microsporum canis, by Candida species, such as Candida albicans, and by Asperaillus species, such as Aspergillus niger.

The new compounds may be administered to the patient by the oral or local route. For oral administration, the compounds are incorporated into pharmaceutically usual compositions, for example in the form of tablets or capsules containing, per daily dosage unit, from about 10 to 750 mg of the active substance, together with a conventional carrier and constitutent. For local administration, for example gels, creams, ointments or suppositories may be used.

Depending on each individual case, the dosage unit comprises an amount of from 5 to 100 mg of a compound of formula I per kilogram of the patient's body weight.

The following Examples illustrate the invention.

EXAMPLE 1: (Method a₁)

1-Methyl-2-(5-nitro-furyl-2-thiomethyl)-5-nitro-imidazole 17.6 Grams (0.1 mol) of 1-methyl-2-chloromethyl-5-nitroimidazole were heated to 50° – 60° C for 1 hour together with 26.7 g (0.1 mol) of 5-nitrofuryl-2-S-isothiouronium hydrobromide in 250 ml of dimethylacetamide in the presence of 10.8 g (0.2 mol) of sodium ethylate. After cooling, about 600 ml of water were added to the reaction mixture until the product had entirely precipitated. The precipitate was suction-filtered and recrystallized from ethanol.

15.4 grams (54% of the theoretical yield) of 1-methyl-2-(5-nitro-furyl-2-thiomethyl)-5-nitro-imidazole were obtained in the form of light-yellow crystals melting at 92° C.

The preparation of 1-methyl-2-chloromethyl-5-nitro-imidazole has been disclosed in German Offenlegungsschrift No. 1,595,929. The preparation of 5-nitrofuryl-2-S-isothiouronium hydrobromide was carried out according to German Offenlegungsschrift No. 2,124,102 from 2-bromo-5-nitro-furan and thio-urea. The isothiouronium compound was used instead of the free but unstable 5-nitro-furyl-mercaptan.

According to the above method, the following compounds were obtained.

1-Methyl-2-(5-nitro-thienyl-2-thiomethyl)-5-nitro-imidazole, m.p. 123° C, from 1-methyl-2-chloromethyl-5-nitro-imidazole (MCNI) and 5-nitro-thienyl-2'-S-isothiouronium hydrobromide; 1-methyl-2-(5-cyano-furyl-2-thiomethyl)-5-nitro-imidazole from MCNI and 5-cyano-furyl-2'-S-isothiouronium hydroiodide; 1-methyl-2-(5-cyano-thienyl-2-thiomethyl)-5-nitro-imidazole from MCNI and 5-cyano-thienyl-2'-S-isothiouronium hydroiodide.

EXAMPLE 2: (Method b₁)

1-Methyl-2-(5-nitro-furyl-2-thiomethyl)-5-nitro-imidazole

To a solution of 25.2 g (0.1 mol) of 1-methyl-2-(S-isothiouronium-methyl)-5-nitro-imidazole hydrochloride in 500 ml of methanol, 10.8 g (0.2 mol) of sodium methylate in 100 ml of methanol were added dropwise while stirring at 0° C, and after 10 minutes, a solution of 19.2 g (0.1 mol) of 2-bromo-5-nitro-furan in 100 ml of methanol was added dropwise at 0° C. After stirring had been continued for 30 minutes, the crystallized precipitate was suction-filtered and recrystallized from ethanol with an addition of charcoal.

Thus, 18.5 g (65% of the theoretical yield) of 1-methyl-2-(5-nitro-furyl-2-thiomethyl)-5-nitro-imidazole were obtained in the form of light-yellow crystals melting at 92° C.

The 1-methyl-2-(S-isothiouronium-methyl)-5-nitro-imidazole hydrochloride used as a starting substance was prepared according to German Offenlegungsschrift No. 2,124,103 by reacting 1-methyl-2-chloromethyl-5-nitro-imidazole (disclosed in German Offenlegungsschrift No. 1,595,929) with thio-urea.

According to the above method, the following compounds were obtained:

1-Methyl-2-(5-nitro-thienyl-2-thiomethyl)-5-nitro-imidazole, m.p. 123° C, from 1-methyl-2-(S-isothiouronium-methyl)-5-nitro-imidazole hydrochloride (MINI) and 2-bromo-5-nitro-thiophene; 1-methyl-2-(5-cyano-furyl-2-thiomethyl)-5-nitro-imidazole from MINI and 2-iodo-5-cyano-furan; 1-methyl-2-(5-cyano-thienyl-2-thiomethyl)-5-nitro-imidazole from MINI and 2-iodo-5-cyano-thiophene.

EXAMPLE 3: (Method a₂)

1-Methyl-2-(methoxy-thiocarbonyl-thiomethyl)-5-nitro-imidazole

To a solution of 17.6 g (0.1 mol of 1-methyl-2-chloromethyl-5-nitro-imidazole in 100 ml of methanol, a solution of 14.6 g (0.1 mol) of potassium methylxanthogenate (potassium salt of dithiocarbonic acid-O-methyl ester) in 80 ml of methanol was added dropwise at 25° C while thoroughly stirring. The reaction was slightly exothermic. The reaction mixture was stirred for 30 minutes at 25° C, then poured onto ice/water, the precipitate was suction-filtered and recrystallized from methanol with an addition of charcoal.

Thus, 17.5 g (71% of the theoretical yield) of 1-methyl-2-(methoxy-thiocarbonyl-thiomethyl)-5-nitro-imidazole were obtained in the form of cream-colored crystals melting at 93° C with decomposition. According to the above method, the following compounds were obtained:

1-Methyl-2-(ethoxy-thiocarbonyl-thiomethyl)-5-nitro-imidazole, m.p. 53° C, from 1-methyl-2-chloromethyl-5-nitro-imidazole (MCNI) and potassium ethyl-xanthogenate;

1-methyl-2-benzoyloxy-thiocarbonyl-thiomethyl)-5-nitro-imidazole from MCNI and potassium benzylxanthogenate;

1-methyl-(2-phenoxy-thiocarbonyl-thiomethyl)-5-nitro-imidazole from MCNI and potassium phenyl-xanthogenate.

The 1-methyl-2-chloromethyl-5-nitro-imidazole used as a starting material was prepared according to German Offenlegungsschrift No. 1,595,929 by reacting 1-methyl-2-hydroxymethyl-5-nitro-imidazole (see German Offenlegungsschrift No. 1,470,102) with thionyl chloride.

EXAMPLE 4: (Method b₂)

1-Methyl-2-(methoxy-thiocarbonyl-thiomethyl)-5-nitro-imidazole

The reaction of 25.2 g (0.1 mol) of 1-methyl-2-(S-isothiouronium-methyl)-5-nitro-imidazole hydrochloride and 11.0 g (0.1 mol) of thiocarbonic acid O-methyl ester chloride in 250 ml of dimethylacetamide in the presence of 10.8 g (0.2 mol) of sodium methylate yielded, upon 1-hour stirring at 50° - 60° C, 13 g (53% of the theoretical yield) of 1-methyl-2-(methoxy-thiocarbonyl-thiomethyl)-5-nitro-imidazole melting at 93° C (decomposition). According to the above method, the following compounds were obtained:

1-Methyl-2-(ethoxy-thiocarbonyl-thiomethyl)-5-nitro-imidazole, m.p. 53° C, from 1-methyl-2-S-isothiouronium-methyl-5-nitro-imidazole hydrochloride (MINI) and thiocarbonic acid O-ethyl ester chloride;

1-methyl-2-(benzyloxy-thiocarbonyl-thiomethyl)-5-nitro-imidazole from MINI and thiocarbonic acid O-benzyl ester chloride;

1-methyl-2-(phenoxy-thiocarbonyl-thiomethyl)-5-nitro-imidazole from MINI and thiocarbonic acid O-phenyl ester chloride.

The 1-methyl-2-(S-isothiouronium-methyl)-5-nitro-imidazole hydrochloride used as a starting material was employed instead of the free unstable 1-methyl-2-mercapto-methyl-5-nitro-imidazole as the mercaptan-yielding agent. The preparation from 1-methyl-2-chloromethyl-5-nitro-imidazole and thio-urea has been disclosed in German Offenlegungsschrift No. 2,124,103.

The thiocarbonic acid O-methyl ester, -O-ethyl ester, -O-benzyl ester and O-phenyl ester chlorides used as starting substances have been obtained according to Helv. chim. acta 6, page 612 (1923).

We claim:
1. 1-Methyl-2-(5-nitro-furyl-2-thiomethyl)-5-nitro-imidazole.
2. 1-Methyl-2-(5-nitro-thienyl-2-thiomethyl)-5-nitro-imidazole.
3. 1-Methyl-2-(methoxy-thiocarbonyl-thiomethyl)-5-nitro-imidazole.
4. 1-Methyl-2-(ethoxy-thiocarbonyl-thiomethyl)-5-nitro-imidazole.

* * * * *